United States Patent [19]
Brown

[11] Patent Number: 5,352,896
[45] Date of Patent: Oct. 4, 1994

[54] HIGH ENERGY RADIATION DETECTOR INCLUDING A RADIATION TO LIGHT CONVERTER HAVING BAFFLE PLATES EXTENDING TOWARD A LIGHT DETECTOR

[75] Inventor: Kevin J. Brown, Crawley, England

[73] Assignee: U.S. Philips Corporation, New York, N.Y.

[21] Appl. No.: 19,529

[22] Filed: Feb. 19, 1993

[30] Foreign Application Priority Data

Feb. 19, 1992 [GB] United Kingdom ............ 9203466.9

[51] Int. Cl.$^5$ ................................................. G01T 1/20
[52] U.S. Cl. ...................................... 250/368; 378/65
[58] Field of Search ................ 378/65, 62, 189, 190; 250/368, 487.1, 366, 367

[56] References Cited

U.S. PATENT DOCUMENTS

| | | | |
|---|---|---|---|
| 3,011,057 | 11/1961 | Anger | 250/366 |
| 4,297,580 | 10/1981 | Juner et al. | 250/368 |
| 4,514,632 | 4/1985 | Barrett | 250/366 |
| 4,829,552 | 5/1989 | Rossi et al. | 378/154 |

FOREIGN PATENT DOCUMENTS

| | | |
|---|---|---|
| 0403802 | 12/1990 | European Pat. Off. |
| 2014301 | 8/1979 | United Kingdom |
| 2212039 | 7/1989 | United Kingdom |

*Primary Examiner*—Carolyn E. Fields
*Attorney, Agent, or Firm*—Jack D. Slobod

[57] ABSTRACT

A radiation converter (1) receives high energy radiation (X) at a first major surface (1a) and emits light (0) from a second major surface (1b). A detector (2) is laterally displaced from the converter (1) so as to be positioned away from the high energy radiation (X). A deflector (3) deflects light emitted by the converter (1) towards the detector (2). A baffle (40) is positioned adjacent the second major surface (1b) of the converter (1). The baffle (40) has an array of baffle plates (4) with light absorbing surfaces (4a) extending transversely of the second major surface (1b) in a direction generally along the optical path (P) to the detector (2). The baffle plates (4) act to absorb light (0′) reflected back to and scattered from the second major surface (1b) so as to reduce the amount of reflected or scattered light (0′) eventually received by the detector enabling an improvement in image contrast.

19 Claims, 2 Drawing Sheets

HIGH ENERGY RADIATION DETECTOR INCLUDING A RADIATION TO LIGHT CONVERTER HAVING BAFFLE PLATES EXTENDING TOWARD A LIGHT DETECTOR

FIELD OF THE INVENTION

This invention relates to apparatus for detecting high energy radiation.

DESCRIPTION OF THE RELATED ART

GB-A-2212039 Describes such apparatus which comprises a radiation converter for receiving high energy radiation at a first major surface and for emitting light from a second major surface opposed to the first major surface, a detector for detecting light emitted by the converter, the detector being laterally displaced from the converter so as to be positioned away from the high energy radiation and a deflector for deflecting light emitted by the converter towards the detector.

Such an apparatus is used in, for example, radiotherapy to enable the position of an area such as a tumour to be treated by the treatment beam to be accurately located relative to reference points of the patient. Although the use of the treatment beam itself may enable more accurate location of the treatment area, the contrast of the radiographic image obtained using high energy penetrating radiation is much lower than that which can be achieved using a diagnostic system such as a low energy X-radiation imaging system because the differences in density of different constituents in the body cause smaller differences in attenuation when high energy radiation is used. These problems are exacerbated by the fact that, when high energy radiation is used, a relatively long path length through the converter is desirable to reduce noise in the output light signal and this will inevitably increase the possibility of scattering and thus of image blurring. Furthermore, as the detector has to be placed out of the line of sight of the high energy radiation, it is necessary to use a deflector such as a mirror arrangement to direct the light output by the converter to the detector and light reflected or scattered back by the deflector onto the second major surface of the converter effectively illuminates the second major surface so increasing the background level detected by the detector and thereby even further reducing the contrast of the image obtained by the detector.

SUMMARY OF THE INVENTION

It is an aim of the present invention to provide apparatus for detecting high energy radiation which allows for an improvement in the contrast of the image obtained by the detector.

According to a first aspect of the present invention, there is provided apparatus for detecting high energy radiation, comprising a radiation converter for receiving high energy radiation at a first major surface and for emitting light from a second major surface opposed to the first major surface, a detector for detecting light emitted by the converter, the detector being laterally displaced from the converter so as to be positioned away from the high energy radiation and a deflector for deflecting light emitted by the converter towards the detector, characterised in that a baffle is positioned adjacent the second major surface of the converter, the baffle comprising an array of baffle plates with light absorbing surfaces extending transversely of the second major surface of the converter in a direction generally along the optical path to the detector.

In apparatus in accordance with the invention, the baffle plates act to absorb light scattered from the second major surface and directly reflected back from the deflector but are located so as to have little effect on the direct light output of the second major surface. Thus, the amount of scattered light eventually received by the detector can be reduced relative to the real signal (that is the direct light output of the converter) so enabling an improvement in the contrast of the image obtained by the detector. The baffle plates may be formed of a plastics material and have matt black surfaces. Such a baffle is easily and cheaply manufactured. The baffle plates are preferably angled relative to the second major surface and to each other so as each lie along the path of the light ray to the detector so that the baffles do not interfere with the real signal reaching the detector. The baffle may be mounted directly to the second major surface of the converter. The deflector may comprise a mirror. Alternatively a more complex system involving the use of mirrors and other optical elements such as lenses may be used.

The converter may comprise a material such as gadolinium oxysulphide ($Gd_2O_2S$) although other materials such as thallium doped sodium iodide (NaI) or tellurium-doped caesium iodide (CsI) or other suitably doped inorganic monocrystalline materials may be used.

Generally the converter comprises a heavy metal, for example stainless steel or copper, screen which provides the first major surface and a fluorescent screen comprising the conversion material such as gadolinium oxysulphide mentioned above. The fluorescent screen should of course be sufficiently thick to provide as great a sensitivity as possible without causing so much scattering that the resolution is unduly reduced. For a gadolinium oxysulphide fluorescent screen then a thickness of about 1 to 2 mm (millimetres) should be suitable while for a thallium-doped NaI or tellurium-doped CsI fluorescent screen then a thickness in the range of 5 mm to 15 mm should be suitable.

The present invention also provides a high energy imaging system comprising a source of high energy radiation, a support for supporting a patient to be irradiated and apparatus in accordance with the first aspect for detecting high energy radiation transmitted through the patient. In a further aspect, the present invention provides a radiotherapy machine comprising a source of high energy radiation, a support for supporting a patient to be irradiated and apparatus in accordance with the first aspect for detecting high energy radiation transmitted through the patient.

It should be understood that, as used herein, the term high energy radiation encompasses X-ray, gamma, electron and other particle radiation capable of being converted into light and having an energy (typically greater than 1 MeV (Mega electron volt)) in the range normally used for treatment of, for example, a tumour rather than for diagnosis of the existence of such a tumour.

The term 'light' is to be considered, in the context of the present Application, to mean electromagnetic radiation in the visible or possibly even the near infra-red region which can be detected by suitable commercially available detectors. The converter should of course have an active element capable of converting the appropriate form of high energy radiation into light detectable by the detector and where, in the present Application, the converter is described as comprising a fluorescent screen, it should be understood that the word 'fluorescent' is used in the interests of brevity and is intended to mean not only those materials which fall within the strict dictionary definition of the term but also those materials normally more precisely described as phosphorescent that is materials where the light output persists after the high energy radiation has been stopped.

It should be noted that GB-A-2014301 describes a channel plate type of scintillator or radiation detector in which the scintillator or converter plates are mounted in a structure having walls and collimator plates coated with an optically reflective material to channel light from the scintillator to the detectors. In one arrangement light from the scintillator may be directed towards the detector by wedge-shaped optical light guides or fibre optic guides. In an alternative arrangement the rear surface of the scintillator plate has a reflective coating and is angled to direct light along a preferred path towards the detectors.

BRIEF DESCRIPTION OF THE DRAWING

Embodiments of the invention will now be described, by way of example, with reference to the accompanying drawings, in which.

DETAILED DESCRIPTION OF THE PREFERRED EMBODIMENT

Figure 1:
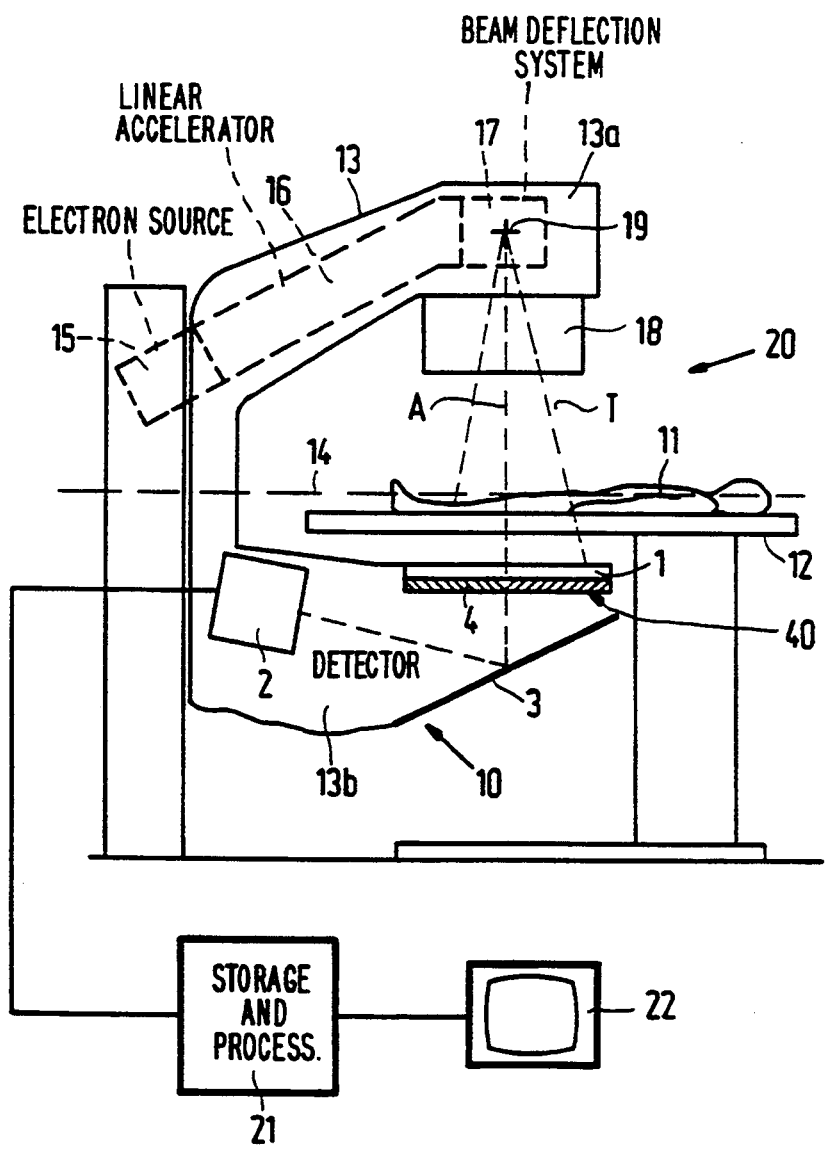
FIG. 1 illustrates diagrammatically and in side-elevation a radiotherapy machine incorporating apparatus in accordance with the invention.

It should of course be understood that the drawings are not to scale and are merely simplified diagrammatic representations and that relative dimensions especially thicknesses of layers may have been exaggerated in the interests of clarity.

Referring now to the drawings, there is illustrated apparatus 10 for detecting high energy radiation, comprising a radiation converter 1 for receiving high energy radiation X at a first major surface 1a and for emitting light 0 from a second major surface 1b opposed to the first major surface 1a, a detector 2 for detecting light 0 emitted by the converter 1, the detector 2 being laterally displaced from the converter 1 so as to be positioned away from the high energy radiation X and a deflector 3 for deflecting light emitted by the converter 1 towards the detector 2. In accordance with the invention a baffle 40 is positioned adjacent the second major surface 1b of the converter 1, the baffle 40 comprising an array of baffle plates 4 with light absorbing surfaces 4a extending tranversely of the second major surface 1b of the converter 1 in a direction generally along the optical path P to the detector 2.

The baffle plates 4 act to absorb light 0' (indicated by dotted lines in FIG. 3) directly reflected back to the second major surface 1b from the deflector 3 and also to absorb light scattered from the second major surface 1b as a result of any reflected light 0' which is not directly absorbed by the baffle plates. Thus, the amount of reflected or scattered light 0' eventually received by the detector can be reduced relative to the real signal (that is the direct light output 0 of the converter 1) so enabling an improvement in the contrast of the image obtained by the detector 2.

Referring now more specifically to the drawings, FIG. 1 illustrates diagrammatically radiotherapy apparatus 20 for irradiating a predetermined region of a patient 11 with a beam T of high energy radiation such as X-rays. The patient 11 is supported on an adjustable table 12. A generally C-shaped gantry 13 rotatable through substantially 360 degrees about a horizontal axis 14, supports, in one arm 13a, an electron source 15, a linear accelerator 16 which accelerates the electrons to a selectable energy typically in the range 4–25 MeV (Mega electron volt), a beam deflection system 17 which deflects the electrons through an angle greater than 90 degrees so that the beam is directed normally towards the axis 14, and a head 18 which includes means for providing a radiotherapy beam of high-energy X-rays produced by causing the electron beam, after deflection, to strike a suitable X-ray target (not shown). The linear accelerator 16 and the beam deflection system 17 are further arranged to bring the electron beam substantially to a point focus 19 which forms the effective point source of the high energy X-ray beam generated by the X-ray target located at the point 19.

The normal radial distance from the source 19 to the horizontal axis 14, i.e. to the isocentre, is typically, 100 cm.

The radiotherapy machine 20 also includes apparatus 10 in accordance with the invention for detecting the high energy radiation X of the treatment beam T to enable an image to be formed of the area to be treated within the patient 11. Where the treatment beam to be used is a high energy (for example 25 MeV) X-ray radiation beam then the treatment beam itself may be used for imaging purposes or the energy of the beam may be somewhat reduced (to for example 6 MeV) for imaging purposes. Imaging may also be carried out at two or more different energies. Where the treatment beam is an electron beam, the imaging may be carried out by using an X-ray radiation beam produced by the same head 18 by moving the X-ray target into the electron beam path to produce the X-ray radiation. A collimator (not shown) in the head 18 may be adjusted to define the high energy radiation beam during imaging.

The converter 1 carrying the baffle 40 is mounted to the other arm 13b of the generally C-shaped gantry 13 so as to be disposed opposite the head 18 on the other side of the patient table 12 thereby enabling the high energy radiation X passing through the patient 11 to be incident on the converter 1. The deflector 3, in this case a mirror extending transversely of, probably generally at between 45° and 60° to, the optical axis A, is also mounted to the other arm 13b of the gantry 13 to deflect light 0 onto the detector 2 which is again mounted in the other gantry arm 13b but laterally spaced away from the optical axis A of the treatment beam T so that the detector 2 is not subject to the high energy radiation X of the treatment beam.

The detector 2 may comprise a video camera, such as a charge-coupled (CCD) solid state silicon camera, with a wide aperture lens, or a two dimensional sensor produced using a thin-film technology. The two-dimensional optical image received by the detector 2 is fed as a sequence of preferably digital pixel point values to a storage and processing means 21 for storing complete images and applying suitable known picture enhancement and processing routines. The means 21 may comprise a suitable digital store e.g. disk drive or semiconductor memory and associated computer suitably programmed. The images thereby produced can then be displayed on a monitor 22 and, if desired, recorded on tape or disc for future reference. As mentioned above the deflector 3 is necessary so that the detector 2 is not subject to incident high energy radiation X which would generate undesired signals therein, and screening, suitably lead, is provided around the detector 2 to attenuate scattered radiation.

Figure 2:
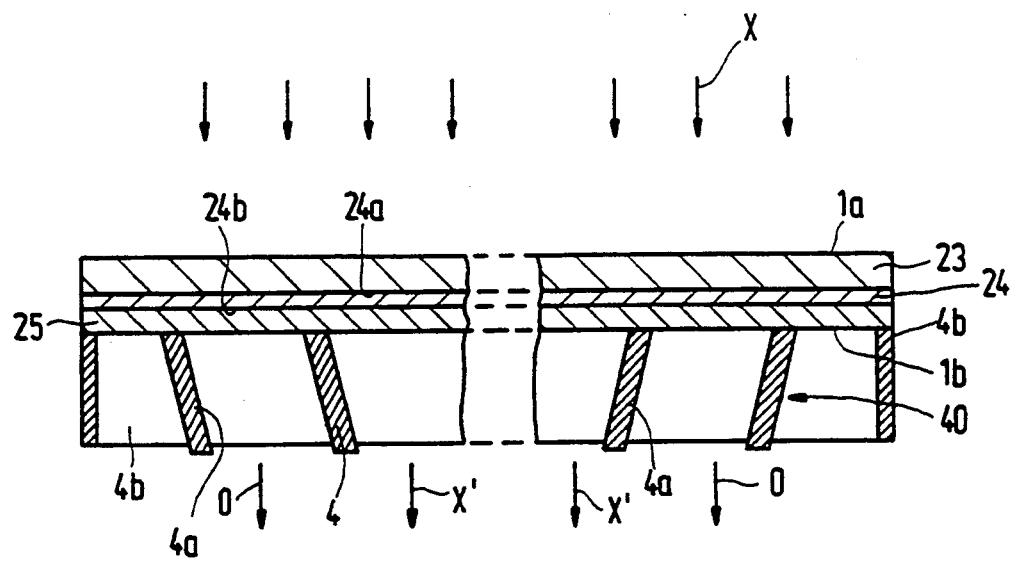
FIG. 2 is a cross-sectional view, part broken away, of a converter and baffle of apparatus in accordance with the invention.

FIG. 2 is a cross-sectional view, with the vertical dimensions exaggerated in the interests of clarity, through a converter 1 suitable for use in apparatus in accordance with the invention.

The converter 1 shown in FIG. 2 comprises a heavy metal screen 23 which provides the first major surface 1a on which the high energy radiation X, in the case discussed above X-ray radiation, is incident.

The heavy metal screen 23 causes incident high energy X-ray radiation to generate, by the process of Compton scattering, energetic electrons which may be more effective than high energy X-ray radiation in causing the converter to emit photons of light. A suitable material for the heavy metal screen 23 is stainless steel. The number of electrons emitted for a given input X-ray radiation flux increases with the thickness and this will correspondingly increase the optical image brightness. However as the thickness increases so does the lateral scattering of the incident ray of radiation and this reduces the image definition. A reasonable compromise is to employ a stainless steel sheet having a thickness in the range of 0.5 mm to 2 mm, for example 1.5 mm. An alternative metal for the heavy metal screen 23 is copper which can give an improved yield of Compton electrons.

In this example, the fluorescent screen 24 is formed of any suitable fluorescent material which is commercially available in a paste form and which can be applied to a support 25 (generally a cardboard support) to form a layer having first and second major surfaces 24a and 24b. The support 25 is secured to the heavy metal screen 23. The active fluorescent ingredient in the paste may be gadolinium oxysulphide ($Gd_2O_2S$).

Of course, any other suitable fluorescent screen could be used and for example the fluorescent material screen could comprise a doped inorganic monocrystalline material such as thallium doped sodium iodide (NaI) or tellurium (t1) doped caesium iodide (CsI). Where such a material is used then the fluorescent screen may together with the heavy metal screen be provided in the form of an optically coupled conversion screen arrangement such as is described in U.K. Patent Application Publication No. 2212039.

The fluorescent screen 24 should of course be sufficiently thick to provide a high light output for a given incident high energy radiation flux but not so thick that the resultant image resolution is unduly marred by scattering. Where a $Gd_2O_2S$ paste fluorescent screen 24 is used, then the screen may be 1 to 2 mm thick. Where a NaI (T1) monocrystalline layer is used to form the fluorescent screen, then it may have a thickness in the range of 5 mm to 15 mm, for example 8 mm.

The baffle 40 is, in the example shown in FIG. 2, mounted by suitable conventional means directly onto the support 25. Alternatively, baffle 40 may be mounted so as to be spaced from the support 25 by, for example, a protective glass plate (not shown).

The baffle 40 comprises, as shown most clearly by FIG. 2, a regular array of baffle plates 4 each of which is relatively thin (typically 0.2 mm) and extends along one dimension of the fluorescent screen 24. In the example illustrated by FIG. 2 the baffle plates 4 extend perpendicularly of the plane of the paper parallel to one another and along the length of the screen 24.

The baffle plates 4 project transversely of the second major surface 24b of the fluorescent screen 24 and typically have a length in this direction of about 2 cm (centimetres). Adjacent baffle plates 4 may be spaced from one another by a similar distance of about 2 cm. The baffle plates 4 may be formed of any suitable material such as cardboard, metal or a plastics material and may be held together by a surrounding frame 4b of similar material which abuts the periphery of the fluorescent screen 24. The frame 4b may be integrally formed with the baffle plates 4. Alternatively, the baffle plates 4 could be secured together by means of transparent supports extending transversely of the baffle plates 4. The surfaces 4a of the baffle plates 4 are arranged to be light absorbing, for example by coating them with a light absorbing material such as a matt black paint.

Figure 3:
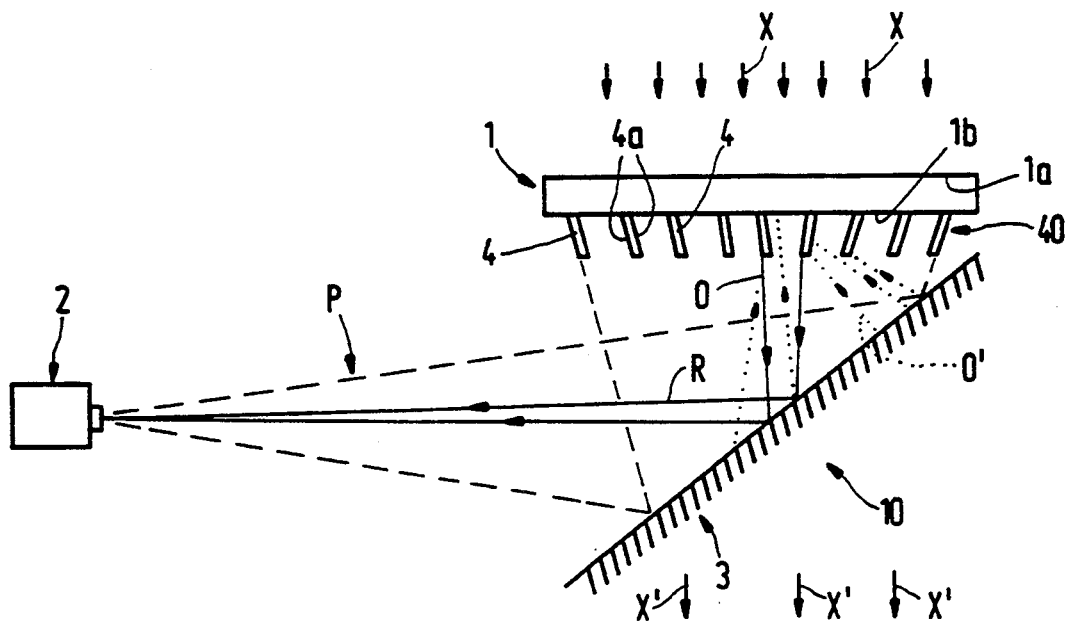
FIG. 3 is a diagrammatic side view of part of the converter, the deflector and detector of apparatus in accordance with the invention for illustrating the operation of the apparatus.

As illustrated most clearly in FIG. 3, the baffle plates 4 do not extend perpendicularly of the second major surface 1b but rather are disposed at an angle to it and to the other baffle plates so as to extend along the lines which a light ray R would follow from the second major surface 1b to the detector 2 via the mirror 3. In this manner the baffle plates 4 present a minimum possible cross-sectional area to the detector 2, so keeping to a minimum any obstruction by the baffle plates of the direct light output from the fluorescent screen 23.

The operation of the apparatus illustrated in FIG. 1 will now be explained by reference to FIG. 2 and FIG. 3 which illustrates very schematically the apparatus 10. In the interests of clarity, the frame of the baffle 40 has been omitted in FIG. 3. High energy radiation, in this example X-rays, X of the treatment beam T which pass through the patient 11 are incident on the first major surface 1a of the converter 1. At least some of the high energy radiation results, by the Compton effect, in the generation of excited electrons in the heavy metal screen 23. These excited electrons pass into the fluorescent screen 24 to cause the emission therefrom of light 0 which is deflected by the mirror 3 to the detector 2 from which, as indicated above, electrical signals representing the detailed image are forwarded for processing and/or storage in the means 21. The detected image may be displayed on the monitor 22. Most of the remaining high energy photons X' pass, as illustrated in FIG. 2 and 3, straight through the fluorescent screen 24 although a very small fraction may cause emission of light (at an efficiency about a thousand times smaller than that of the electrons) from the fluorescent screen 24.

Although most of the light 0 emitted by the fluorescent screen 24 is deflected by the mirror 3 towards the detector 2 some light 0' (indicated by the dotted lines in FIG. 3 where the solid lines indicate light ray paths R of the light 0 to the detector 2 and the dashed lines P indicate the cone of acceptance of the detector 2) may be reflected back from the mirror 3 towards the fluorescent screen 1. If such reflected light 0' were incident on the fluorescent screen 1 it would be scattered and would effectively illuminate the fluorescent screen thereby increasing the background light level and so reducing the image contrast. However, as indicated in FIG. 3, the baffle plates 4 act to absorb the majority of the light 0' reflected back from the mirror 3 so that it does not reach the fluorescent screen 1. This enables the contrast of the image to be improved.

Although in the example described above, a single detector 2 is used, the detector may consist of an array of separate detector elements. Also, the deflector 3 may consist, as described above, simply of a mirror 3 or a more complicated optical system involving lenses etc. may be used. The mirror 3 itself could be replaced by a deflecting prism or lens arrangement.

The high energy radiation detecting apparatus described above may be used in areas outside the radiotherapy field, for example in equipment for detecting flaws or holes by means of high energy radiation.

From reading the present disclosure, other modifications and variations will be apparent to persons skilled in the art. Such modifications and variations may involve other features which are already known in the design, manufacture and use of radiotherapy systems and high energy radiation detecting apparatus and component parts thereof and which may be used instead of or in addition to features already describes herein. Although claims have been formulated in this application to particular combinations of features, it should be understood that the scope of the disclosure of the present application also includes any novel feature or any novel combination of features disclosed herein either explicitly or implicitly, whether or not it relates to the same invention as presently claimed in any claim and whether or not it mitigates any or all of the same technical problems as does the present invention. The applicants hereby give notice that new claims may be formulated to such features and/or combinations of such features during the prosecution of the present application or of any further application derived therefrom.

I claim:

1. Apparatus for detecting high energy radiation, comprising a radiation converter for receiving high energy radiation at a first major surface and for emitting light from a second major surface opposed to the first major surface, a detector for detecting light emitted by the converter, the detector being laterally displaced from the converter so as to be positioned away from the high energy radiation and a deflector for deflecting light emitted by the converter towards the detector, characterised in that a baffle is positioned adjacent the second major surface of the converter, the baffle comprising an array of baffle plates with light absorbing surfaces extending transversely of the second major surface of the converter in a direction generally along the optical path to the detector.

2. Apparatus according to claim 1, further characterised in that the baffle plates are formed of a plastics material and have matt black surfaces.

3. Apparatus according to claim 2, further characterised in that the baffle plates are angled relative to the second major surface and to each other so as each to lie along the path of a light ray to the detector.

4. Apparatus according to claim 3, further characterised in that the baffle is mounted to the second major surface of the converter.

5. Apparatus according to claim 4, further characterised in that the deflector comprises a mirror.

6. Apparatus according to claim 5, further characterised in that the converter comprises a doped inorganic monocrystalline material.

7. Apparatus according to claim 6, further characterised in that the inorganic monocrystalline material comprises a material selected from the group consisting of sodium and cesium iodide.

8. Apparatus according to claim 2, further characterised in that the baffle is mounted to the second major surface of the converter.

9. Apparatus according to claim 2, further characterised in that the deflector comprises a mirror.

10. Apparatus according to claim 2, further characterised in that the converter comprises a doped inorganic monocrystalline material.

11. Apparatus according to claim 2, further characterised in that the converter comprises gadolinium oxysulphide.

12. Apparatus according to claim 1, further characterised in that the baffle plates are angled relative to the second major surface and to each other so as each to lie along the path of a light ray to the detector.

13. Apparatus according to claim 1, further characterised in that the baffle is mounted to the second major surface of the converter.

14. Apparatus according to claim 1, further characterised in that the deflector comprises a mirror.

15. Apparatus according to claim 1, further characterised in that the converter comprises a doped inorganic monocrystalline material.

16. Apparatus according to claim 15, further characterised in that the inorganic monocrystalline material comprises a material selected from the group consisting of sodium iodide and cesium iodide.

17. Apparatus according to any one of claim 1, further characterised in that the converter comprises gadolinium oxysulphide.

18. Apparatus according to claim 1, further characterised in that the converter comprises a metal screen providing the first major surface and a fluorescent screen.

19. A high energy imaging irradiating system comprising a source of high energy radiation, a support for supporting a patient to be irradiated by said source and means for detecting high energy radiation transmitted through the patient, comprising a radiation converter for receiving high energy radiation at a first major surface and for emitting light from a second major surface opposed to the first major surface, a detector for detecting light emitted by the converter, the detector being laterally displaced from the converter so as to be positioned away from the high energy radiation and a deflector for deflecting light emitted by the converter towards the detector, wherein a baffle is positioned adjacent the second major surface of the converter, the baffle comprising an array of baffle plates with light absorbing surfaces extending transversely of the second major surface of the converter in a direction generally along the optical path to the detector.

* * * * *